(12) United States Patent
Cran (10) Patent No.: US 11,389,332 B2
(45) Date of Patent: Jul. 19, 2022

(54) NOISE-CANCELLING EAR PLUGS

(71) Applicant: Make Great Sales Limited, Wanchai (HK)

(72) Inventor: Bruce Cran, Richmond (CA)

(73) Assignee: Make Great Sales Limited, Hong Kong (HK)

( * ) Notice: Subject to any disclaimer, the term of this patent is extended or adjusted under 35 U.S.C. 154(b) by 234 days.

(21) Appl. No.: 16/713,811

(22) Filed: Dec. 13, 2019

(65) Prior Publication Data

US 2020/0188176 A1 Jun. 18, 2020

Related U.S. Application Data

(63) Continuation-in-part of application No. 16/661,619, filed on Oct. 23, 2019, now abandoned.

(60) Provisional application No. 62/781,397, filed on Dec. 18, 2018.

(51) Int. Cl.
*A61F 11/08* (2006.01)
*G10K 11/04* (2006.01)
*A61F 11/04* (2006.01)

(52) U.S. Cl.
CPC ............ *A61F 11/04* (2013.01); *G10K 11/04* (2013.01); *A61F 11/085* (2022.01)

(58) Field of Classification Search
CPC .......... A61F 11/04; A61F 11/06; A61F 11/08; A61F 2011/085; G10K 11/04
See application file for complete search history.

(56) References Cited

U.S. PATENT DOCUMENTS

| | | | | |
|---|---|---|---|---|
| 3,842,829 A | * | 10/1974 | Ellis | A61F 11/08 |
| | | | | 128/868 |
| 4,540,063 A | * | 9/1985 | Ochi | A61F 11/08 |
| | | | | 128/867 |
| 4,582,053 A | | 4/1986 | Wilson | |
| 5,355,418 A | | 10/1994 | Kelsey et al. | |
| 6,068,079 A | * | 5/2000 | Hamery | A61F 11/08 |
| | | | | 128/864 |
| 6,148,821 A | * | 11/2000 | Falco | H04R 1/1016 |
| | | | | 128/864 |
| 7,025,061 B2 | | 4/2006 | Haussmann | |
| 7,512,243 B2 | | 3/2009 | Haussmann | |
| 7,512,247 B1 | | 3/2009 | Odinak et al. | |

(Continued)

FOREIGN PATENT DOCUMENTS

| | | | | |
|---|---|---|---|---|
| CN | 108272554 A | * | 7/2018 | |
| EP | 2439734 A1 | * | 4/2012 | ............. A61F 11/08 |

(Continued)

*Primary Examiner* — Edgardo San Martin
(74) *Attorney, Agent, or Firm* — Cochran Freund & Young, LLC; William O'Meara (57) ABSTRACT

A noise-cancelling earplug assembly is provided, having an ear piece for insertion into the ear canal and a housing removably attached to the ear piece. A hollow core is defined in the housing to receive a sound-selective sound barrier that contains at least one sound filtering element to attenuate sounds reaching the ear drum. An end cap is provided and is attachable to the housing to enclose the sound-selective sound barrier inside the housing. The sound selective sound barrier can be removed from the housing of the earplug and replaced with a different sound selective sound barrier with different sound attenuation characteristics.

17 Claims, 12 Drawing Sheets

(56) References Cited

U.S. PATENT DOCUMENTS

| | | | | |
|---|---|---|---|---|
| 8,054,985 B2 * | 11/2011 | Doty | ................. | A61F 11/08 |
| | | | | 381/72 |
| 10,375,467 B2 * | 8/2019 | Xu | ................. | H04R 3/04 |
| 10,779,992 B2 * | 9/2020 | Delfino | ................. | A61F 11/08 |
| 2005/0087195 A1 * | 4/2005 | Huang | ................. | A61F 11/08 |
| | | | | 128/864 |
| 2009/0080670 A1 | 3/2009 | Solbeck et al. | | |
| 2010/0307859 A1 * | 12/2010 | Lopez | ................. | A61F 11/08 |
| | | | | 181/129 |

FOREIGN PATENT DOCUMENTS

| | | | | | |
|---|---|---|---|---|---|
| FR | 2680463 | A1 * | 2/1993 | ............. | A61F 11/08 |
| FR | 2867063 | A1 * | 9/2005 | ............. | A61F 11/08 |
| FR | 2997010 | A1 * | 4/2014 | ............. | A61F 11/06 |
| SU | 740245 | A1 * | 6/1980 | ............. | A61F 11/08 |

\* cited by examiner

NOISE-CANCELLING EAR PLUGS

RELATED APPLICATIONS

This application claims priority from U.S. Provisional Patent Application No. 62/781,397 filed on Dec. 18, 2018 entitled "NOISE-CANCELLING EAR PLUGS", and U.S. Non-Provisional patent application Ser. No. 16/661,619 filed on Oct. 23, 2019 entitled "NOISE-CANCELLING EAR-PLUGS". This application claims the benefit under 35 USC § 119 of U.S. Provisional Patent Application No. 62/781,397 filed Dec. 18, 2018 entitled "NOISE-CANCELLING EAR PLUGS", and the benefit under 35 USC § 120 of U.S. Non-Provisional patent application Ser. No. 16/661,619 filed on Oct. 23, 2019 entitled "NOISE-CANCELLING EAR-PLUGS", which are incorporated herein by reference in their entirety.

TECHNICAL FIELD

The present disclosure relates generally to devices that provide hearing protection, and more particularly to earplugs with selective sound attenuation.

BACKGROUND

Prolonged and repeated exposure to high volume or high intensity sounds can cause discomfort and may lead to permanent hearing loss over time. Workers at construction sites, for example, may be exposed to excessive sound amplitudes as a result of operating various machines and tools like jack hammers and electric saws. In other situations, excess background noise can reduce or impair the ability of a person to hear specific sounds. For example, in an airplane, it may be difficult hear another person speak because of the sustained low frequency drone produced by the plane's engines.

To address these problems, earplugs may be used to block excessively loud or undesired sounds. While such earplugs can attenuate the volume of sound, the sound attenuation may result in attenuation of sounds that the user may want to hear, such as verbal communication. Active noise cancelling earplugs may be used to provide selective attenuation of certain sounds. However, active components require a power source and computing elements to actively generate a suitable noise cancelling signal. As such, active earplugs may be expensive, bulky and heavy.

Accordingly, in view of these and other deficiencies, there is a need for an earplug that addresses the above-noted disadvantages of existing earplugs and can be customized for the needs of the user to provide the desired sound attenuation and comfort.

SUMMARY OF THE DISCLOSURE

In general, the present specification describes a passive earplug with selective sound attenuation.

One aspect of the invention provides an earplug assembly for insertion into an ear canal of a user. The earplug assembly includes an ear piece comprising a first end shaped for insertion into the ear canal, and an opposing second end. Sounds enter through the opposing second end. The ear piece may be resiliently deformable. A housing is also provided that is removably attached to the second end of the ear piece. The housing has a hollow core.

In particular embodiments, the hollow core is adapted to receive a sound-selective sound barrier. The sound barrier includes at least one sound filtering element, such as at least one of a solid and liquid sound attenuator. The solid attenuator may include a solid disc-shaped or solid spherical sound attenuator.

In some embodiments, the earplug assembly includes an end cap attachable to the housing to enclose the sound-selective sound barrier inside the housing, wherein the housing is positioned between the ear piece and the end cap.

In other embodiments, the sound-selective sound barrier includes a cartridge enclosing the at least one sound filtering element, the cartridge being removable from the housing. The cartridge may include a magnetic plate portion attachable to a magnetic cartridge removal wand.

In other embodiments, the hollow core of the ear piece is adapted to receive a sound-selective sound attenuating capsule. The sound attenuating capsule may be selected from a plurality of interchangeable sound attenuating capsules having different attenuation profiles. For example, the sound attenuating capsule may be selected from one of: a fiber tube capsule adapted for absorbing sound, the fiber tube capsule having a foam core; an inverted baffle cone having two cone portions arranged in an hour-glass structure, each cone portion having an acoustic channel extending from an end face to a side face of the cone portion; and a combination capsule including a combination of at least one solid filtering element (such as one or more rigid filter plates) and at least one liquid sound filtering element (such as oil) enclosed within a capsule body.

Additional aspects of the present invention will be apparent in view of the description which follows.

BRIEF DESCRIPTION OF THE DRAWINGS

Features and advantages of the embodiments of the present invention will become apparent from the following detailed description, taken with reference to the appended drawings in which.

DETAILED DESCRIPTION

The description which follows, and the embodiments described therein, are provided by way of illustration of examples of particular embodiments of the principles of the present invention. These examples are provided for the purposes of explanation, and not limitation, of those principles and of the invention.

Referring first to FIG. 1, shown therein is a perspective view (FIG. 1A) and corresponding cross-section view (FIG. 1C), and an exploded perspective view (1B) with corresponding exploded plan view (FIG. 1D) of a sound attenuating earplug assembly 100. The earplug assembly 100 shown is generally provided or presented to a user as a pair of sound attenuating earplugs. Each earplug is intended for insertion in to the ear canal of the user to attenuate sounds of particular frequencies.

In the FIG. 1 embodiment, the earplug assembly 100 includes an ear piece 110, an end cap 150 and a housing 130 containing one or more sound filtering elements 132. The ear piece 110 is intended for insertion into the ear canal. When assembled as shown in FIGS. 1A and 1C, the housing 130 is positioned and attached between the ear piece 110 and the end cap 150 using one or more various attachment mechanisms. Housing 130, ear piece 110 and end cap 150 are arranged along a longitudinal axis 160. The different components are arranged generally, but not necessarily always, symmetrically about the longitudinal axis 160. Symmetry may ease placement or insertion. However, in other embodiments, an asymmetrical design or arrangement enables the user to orient the earplug assembly 100 in a particular desired position in the outer ear. When the earplug assembly 100 is inserted into the ear of the user, the sound filtering elements 132 contained in the housing 130 selectively attenuate sound and thereby reduce the intensity of certain sounds stimulating the ear drum. The earplug assembly 100 can be fabricated to be relatively compact. In some embodiments, when the earplug assembly 100 is fully inserted into the ear canal of the user, about no more than 1 to 2 cm of the earplug assembly 100 extends out from the ear canal.

In particular embodiments, the ear piece 110 is made using a soft and resilient material for ease of insertion into the ear canal and to provide user comfort. Example materials include foam, silicon, polyurethane (PU or PUR), rubber and the like. When the earplug assembly 100 is inserted into the user's ear canal, the ear piece 110 makes contact with the inner surface of the ear canal. In the FIG. 1 embodiment, the diameter or width of the ear piece 110 along a transverse axis x that is orthogonal to longitudinal axis 160 can be chosen to be sufficiently large so that the soft and resilient material of the ear piece 110 is compressed as the ear piece 110 is pushed into the ear canal. Deformation of the ear piece 110 material creates friction and resistance to movement between the ear piece 110 and the inner surface of the ear canal as the compressed material of the ear piece 110 attempts to expand and revert to its relaxed state. As a result, earplug assembly 100 remains snugly inserted in the ear canal during use, but can be pulled out by the user when the earplug is no longer needed. The expansion of the soft and resilient material of the ear piece 110 establishes an acoustic seal circumferentially around the ear canal, separating the inner ear (e.g. the ear drum and cochlea) from the outside environment. Accordingly, all or a substantial amount or all of the sound waves that enter the ear canal must traverse the earplug assembly 100 through the sound filtering elements 132.

In the FIG. 1 embodiment, the ear piece 110 has a generally hemispherical shape with a rounded or curved surface at the insertion or leading end 112 of the ear piece 110. Even with a hemispherical shape, the degree of roundness or curvature can be varied to adjust for comfort and/or snugness. For example, FIGS. 1A, 1B and 1E shows hemispherical ear piece 110 with more rounding (i.e. higher radius of curvature) as compared to the hemispherical shape shown in FIGS. 1C and 1D which presents a relatively smaller degree of rounding (i.e. lower radius of curvature) making the latter to appear less spherical. In other embodiments, the ear piece 110 can be formed in a cylindrical or conical bullet-like shape in which the ear piece 110 is narrower at the insertion end 112 so as to provide a tapered profile. In the embodiment of FIG. 1, the ear piece 110 includes a cavity 114 to receive a rigid attachment stem 134 of the housing 130. In some embodiments, the diameter of the cavity 114 is smaller than the diameter of ridged attachment stem 134 so that insertion of the attachment stem 134 into the cavity 114 causes the resilient ear piece material surrounding the cavity 114 to deform and compress onto the attachment stem 134. This compression produces friction and resists movement between the housing 130 and the ear piece 110 and allows the ear piece 110 to be removed from the housing 130 when desired, for example, for cleaning or replacement.

In certain embodiments, the attachment stem 134 has one or more ridges 138 extending radially therefrom to keep the ear piece 110 and the housing 130 together in place (e.g. as seen in the FIG. 1 embodiment). The ridges can also be useful in reducing the friction between the cavity 114 and attachment stem 134 to allow easier separation of the ear piece 110 and the housing 130. In some embodiments, the ridges can be used to create secondary cavities or pockets 140 to provide additional acoustic filtering. Other embodiments omit ridges 138.

As seen in FIG. 1, the cavity 114 can extend along longitudinal axis 160 to create a channel or tunnel extending through the entire ear piece 110. This tunnel can help to improve transmission of sounds that are able to pass through sound filtering elements 132 contained in housing 130. In other embodiments, the cavity does not extend through all of ear piece 110. For example, in certain embodiments the cavity 114 penetrates partially into the body of the ear piece 110 by a depth which is equal to the length of the attachment stem 134.

The housing 130 includes a hollow core 136 for placement of a sound-selective sound barrier 131 containing one or more sound filtering elements 132. In the FIG. 1 embodiment, the sound barrier 131 is in the form of a cartridge container (i.e. sound barrier cartridge) for holding the sound filtering elements 132 in place. In other embodiments, the sound barrier 131 does not include a container and is defined by the positioning of sound filtering elements 132 directly within core 136 region of the housing 130.

Figure 1A:
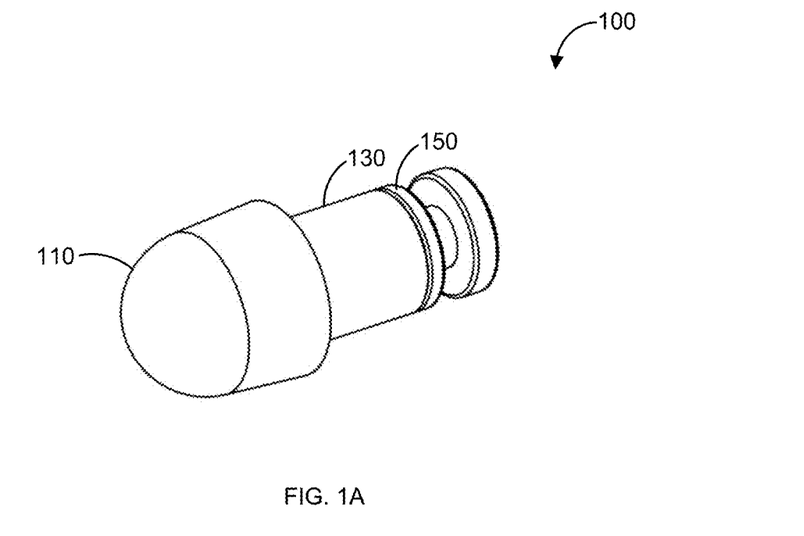
FIGS. 1A, 1B, 1C, 1D and 1E (collectively, FIG. 1) show a perspective assembled view, an exploded perspective view, a first cross-section view, an exploded plan view, and a second cross-section view, respectively, of a sound attenuating earplug assembly in accordance with at least one embodiment.
Figure 1B:
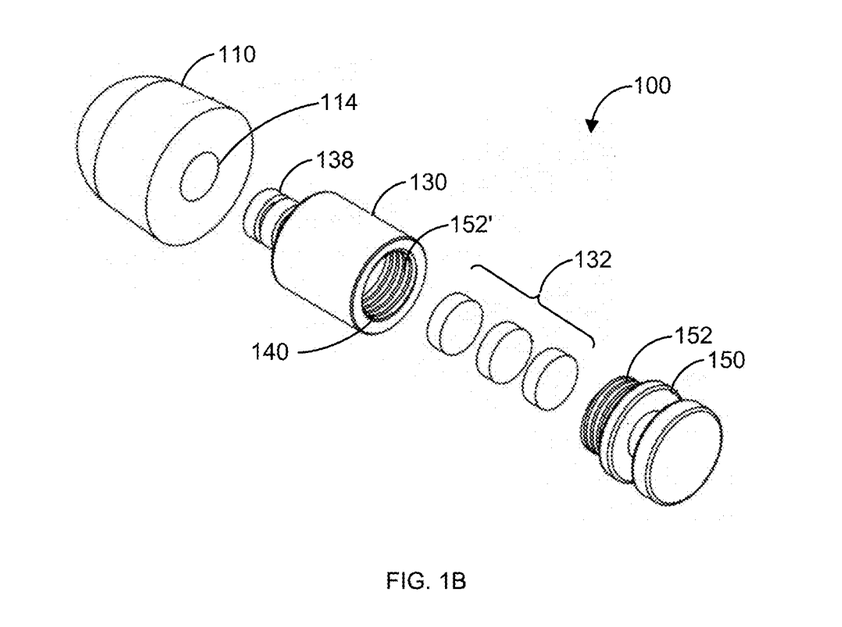
Figure 1C:
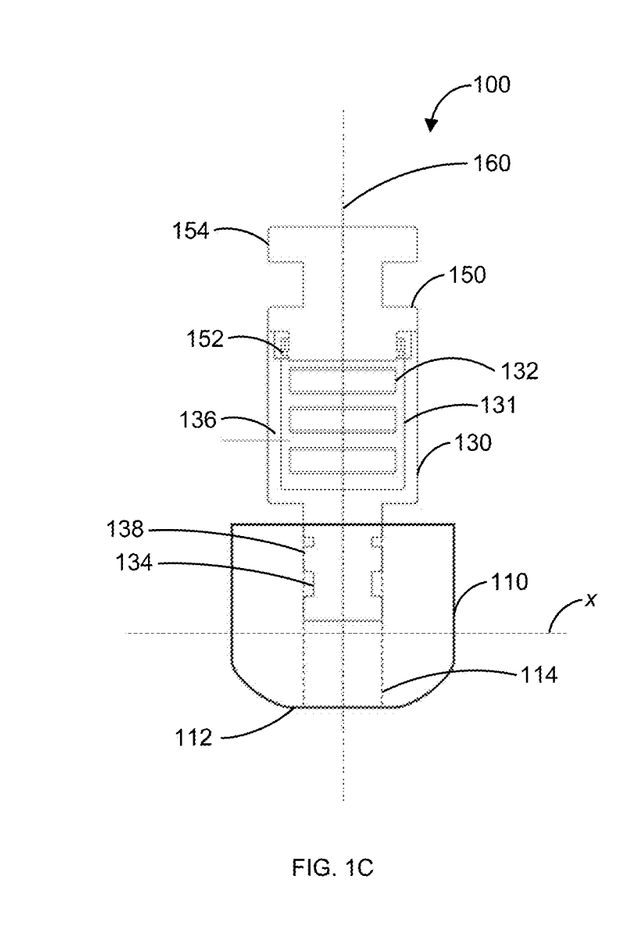
Figure 1D:
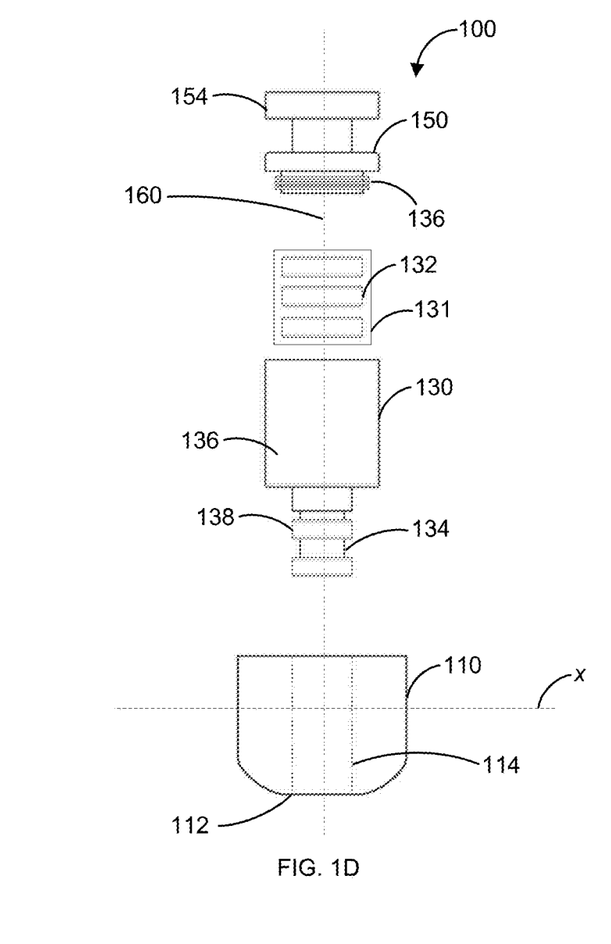
Figure 1E:
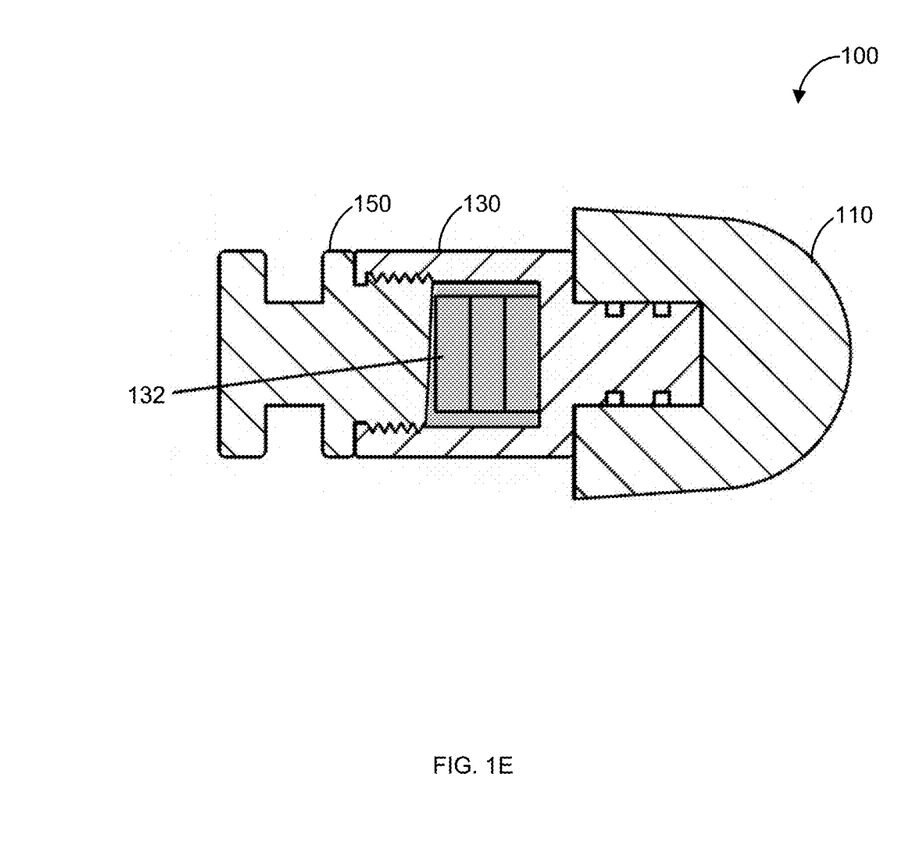

As noted previously, the sound filtering elements 132 are provided to attenuate sounds of particular frequencies. The sound filtering elements 132 can include various filtering media such as a liquid sound filter medium, a solid sound filter medium, or a combination of solid and liquid sound filtering media. For example, the earplug assembly 100 of FIG. 1E shows an embodiment with a liquid sound filtering medium represented by the darkened region. The acoustic properties of each sound filter medium characterize its frequency response, which determine the frequencies that the sound filter medium is capable of attenuating. Different sound filtering media can be combined to obtain the desired overall sound filtering characteristics or profile. For example, where the earplug assembly 100 is intended to be used at a construction site where there is considerable undesirable sound at high and low frequency ranges, such as those produced by high-power construction tools, a combination of filtering media each capable of attenuating sounds at the targeted high and low frequencies can be used. The choice of filtering media in this case produces a "bandpass" filter profile that allows transmission of mid-range frequencies corresponding to voice sounds (i.e. speech) to pass through the sound-selective barrier 131 to reach the ear drum.

In the FIG. 1 embodiment, a number of disc-shaped solid filter media are used as the sound filtering elements 132. The disc-shaped media can be stacked together to form the sound barrier 131. In some embodiments, each disc can be made of the same material, each providing the same attenuation characteristics. The magnitude of attenuation can be increased or decreased by adding or removing discs. In other embodiments, at least one of the discs has different sound attenuation characteristics so that combining such discs with the other discs produces a more varied filtering profile.

In other embodiments, solid filter media can be in other shapes and vary in size. For example, a solid filter medium can take the form of irregularly shaped particles or uniformly shaped particles such as spheres. In some embodiments, the solid disc or particle medium can be surrounded by a further, liquid medium. The types of materials used for the solid and liquid medium can be any suitable sound attenuating material. For example, suitable solid materials can include, but are not limited to, any one or a combination of stone, metal, amalgam, ceramic, and plastic. Suitable liquid materials can include, but are not limited to, any one or a combination of water or water-based liquids of various viscosities, oil or oil-based liquids of various viscosities, and various organic or inorganic liquid compounds. The use of different materials provide a customized or "tuned" sound barrier 131 capable of attenuating different sound frequencies. As such, any combination of materials can be combined to obtain a desired sound absorption/attenuation characteristic to provide a desired acoustic experience. This level of customization is an improvement over earplugs that are made of only one material. Furthermore, the disclosed earplug assembly 100 operates passively, without the use of active electronics as in the case of powered sound cancelling earplugs, thereby allowing the earplug assembly 100 to be light and compact.

The sound barrier 131 and associated sound filtering elements 132 can be enclosed in the housing 130 with the end cap 150. The end cap 150 of the present embodiment includes a threaded securement mechanism 152 to attach the end cap 150 to an opening 140 (FIG. 1B) of the housing 130, the opening 140 being provided with corresponding threads 152' for engaging with the threads 152 of the end cap 150. In the present embodiment, the threading is positioned inside of the housing 130. However, in other embodiments, such as the embodiment of FIGS. 4A to 4F, the threading may be provided on the outside. The use of the end cap 150 enables the sound barrier 131 to be securely enclosed inside the housing 130. This is useful where the sound filtering medium includes a liquid material, as the end cap 150 would prevent the liquid material from leaking. Additionally, the end cap 150 allows for easier insertion and/or removal of the earplug assembly 100. For example, various suitable designs can be implemented on the end cap 150 so as to allow a user of the earplug assembly 100 to grab or hold onto the end cap to insert or remove earplug assembly 100 into and out of the ear canal. For instance, end cap 150 shown in FIGS. 1C and 1D is provided with a plate-shaped or disc-shaped structure 154 to allow it to be grasped by the user. Other shapes and structures for end cap 150 can include a fan or fin shape, or a stem shape.

Figure 2A:
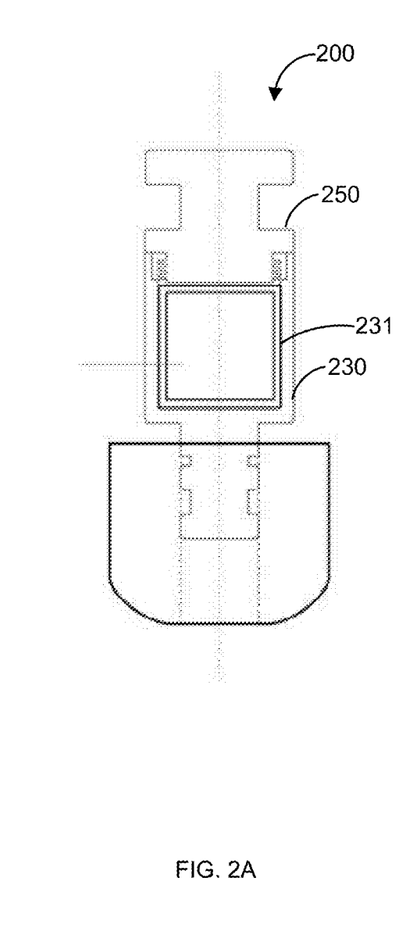
FIGS. 2A and 2B (collectively, FIG. 2) show a cross-section view and an exploded plan view, respectively, of a sound attenuating earplug assembly according to another embodiment.
Figure 2B:
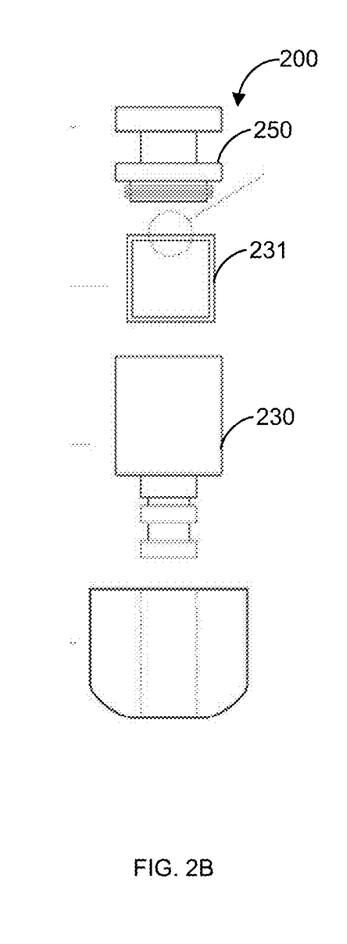

Referring now to FIG. 2, shown therein is an embodiment of an earplug assembly 200 with a removable end cap 250 and a removable sound barrier cartridge 231 in an assembled view (FIG. 2A) and corresponding exploded view (FIG. 2B). Elements illustrated in FIG. 2 that are similar to those in FIG. 1 are similarly numbered for ease of reference. The removable end cap 250 and sound barrier cartridge 231 allow a user to remove the sound barrier cartridge 231 via an opening (not shown) in the housing 230. Upon replacement with a new barrier cartridge, the new cartridge can be secured by closing the opening with the end cap 250. The removability of the sound barrier cartridge 131 thereby allows the user to change the acoustic characteristics (i.e. the sound attenuation profile) of earplug assembly 200 as desired. For example, the sound barrier cartridge 231 containing a first set of sound filtering elements can be removed and replaced with a different cartridge containing a different set of sound filtering elements. Doing so allows the user to filter out different kinds of sound frequencies, for different circumstances.

Figure 3A:
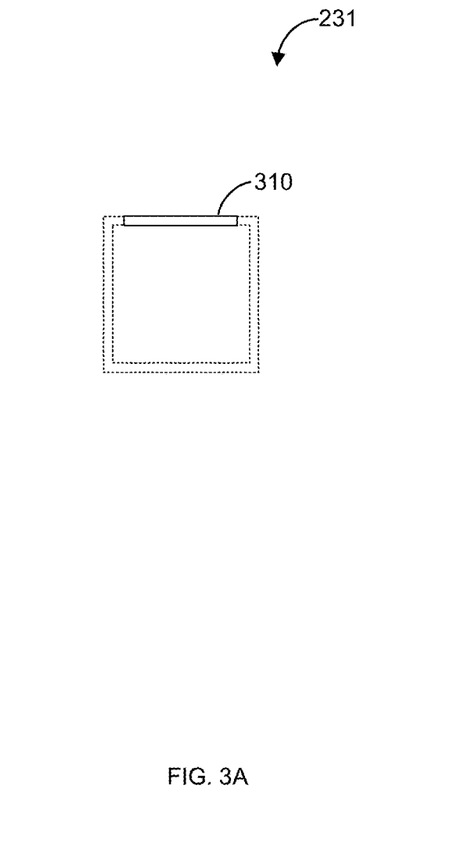
FIGS. 3A and 3B (collectively, FIG. 3) show a removable sound barrier cartridge and corresponding cartridge removal wand.
Figure 3B:
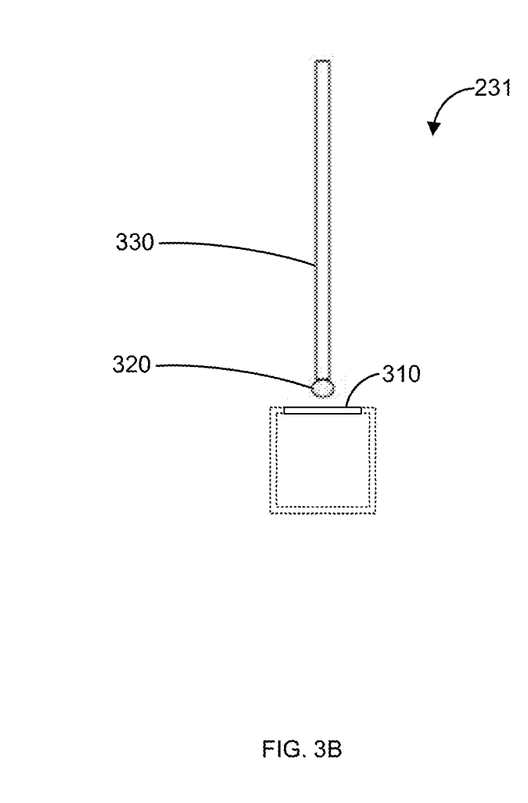

FIG. 3 shows one embodiment of the removable sound barrier cartridge 231 (FIG. 3A) and a corresponding cartridge removal wand 330 (FIG. 3B). In the FIG. 3 embodiment, the sound barrier cartridge 231 includes a magnetic plate 310 on one side. The magnetic plate can be magnetically attached to a magnet 320 positioned at the tip of the cartridge removal wand 330. The use of a magnet of suitable strength gives a user the ability to pull the sound barrier cartridge 231 out of the housing 230 with the cartridge removal wand 330 and remove the sound barrier cartridge 231 from the housing 230. A new cartridge can be positioned into the housing 230 using the same cartridge removal wand 330 by pushing the sound barrier cartridge 231 into the housing 230. The magnetic plate 310 can also be used as a positional indicator to indicate to the user that when the barrier cartridge 231 is properly oriented to provide sound filtering, the magnetic plate 310 faces the end cap 250 and is accessible via the opening of the housing 230. The positional indicator allowing proper orientation of the sound barrier cartridge is useful where the sound filtering elements in the sound barrier cartridge 231 must be positioned/arranged in a particular order to obtain the desired sound attenuation/filtering. In other embodiments, forceps can be used to remove the sound barrier cartridge instead of the cartridge removal wand 330. The sound barrier, for example, can include receptacles to receive the pointed ends of the forceps.

Referring now to FIG. 4, shown therein are exploded perspective views of an embodiment of an earplug assembly 400 with interchangeable noise reduction or sound attenuating capsules. Elements illustrated in FIG. 4 that are similar to those in FIGS. 1 and 2 are similarly numbered for ease of reference. Similar to the earplug assemblies 100 and 200 of FIGS. 1 and 2, the earplug assembly 400 of the present embodiment includes an ear piece 410, re-sealable housing 430 for receiving an interchangeable sound attenuating capsule 432, and a removable end cap 450. The sound attenuating capsules, as described in greater detail below, can be configured to attenuate or filter specific sound frequencies so that its corresponding filtering profiles may be tuned for desired applications and uses.

In the present embodiment, defined in the ear piece 410 is a cavity 414 (see FIG. 4A) that extends longitudinally through the ear piece 410 to an opening 416 (see FIG. 4B) at an insertion end of the ear piece 410. Since opening 416 is located at the end of the ear piece 410 that makes contact with the user's ear, opening 416 may be referred to as the proximal opening. The proximal opening 416 can provide improved sound transmission over designs that do not include such an opening. The ear piece 410 is attachable to the housing 430 by inserting an attachment stem 434 of the housing 430, shown in FIG. 4B, into the cavity 414 of the ear piece 410. Similar to the assembly 100 of FIG. 1, the attachment stem 434 can include one or more ridges 438 that extend radially therefrom. The ridges 438 may provide similar benefits to the ridges 138 described in the FIG. 1 embodiment.

Figure 4A:
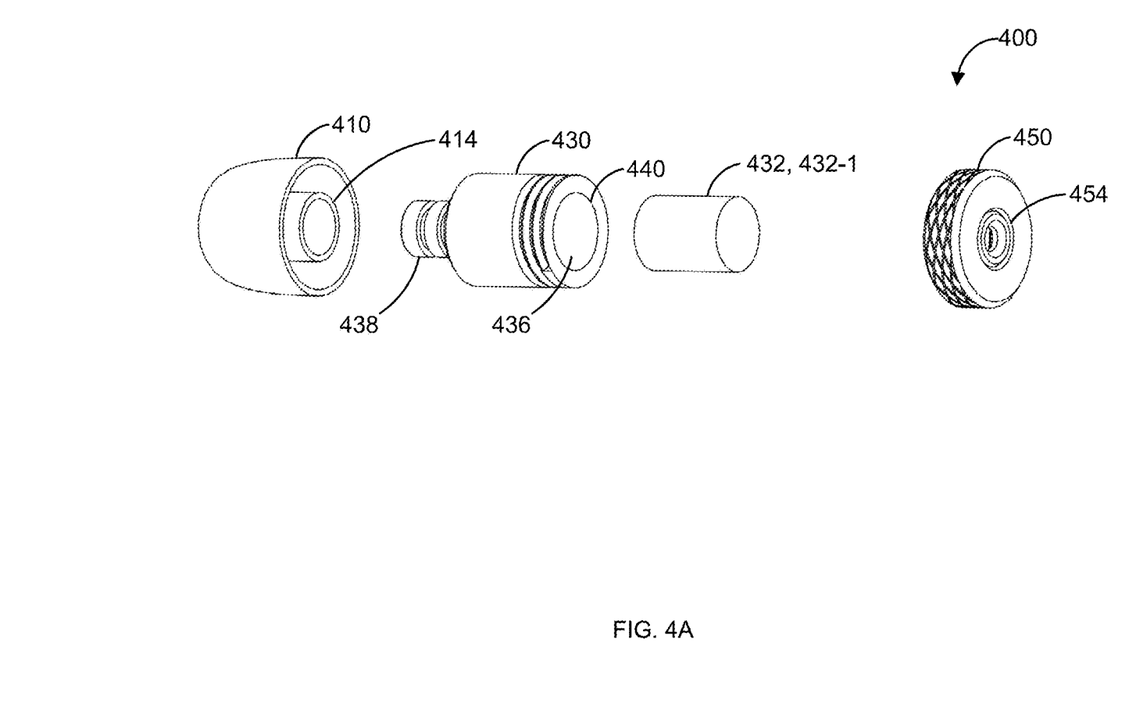
FIGS. 4A, 4B, 4C, 4D, 4E and 4F (collectively, FIG. 4) show an earplug assembly according to one embodiment with interchangeable noise reduction or sound attenuating capsules.
Figure 4B:
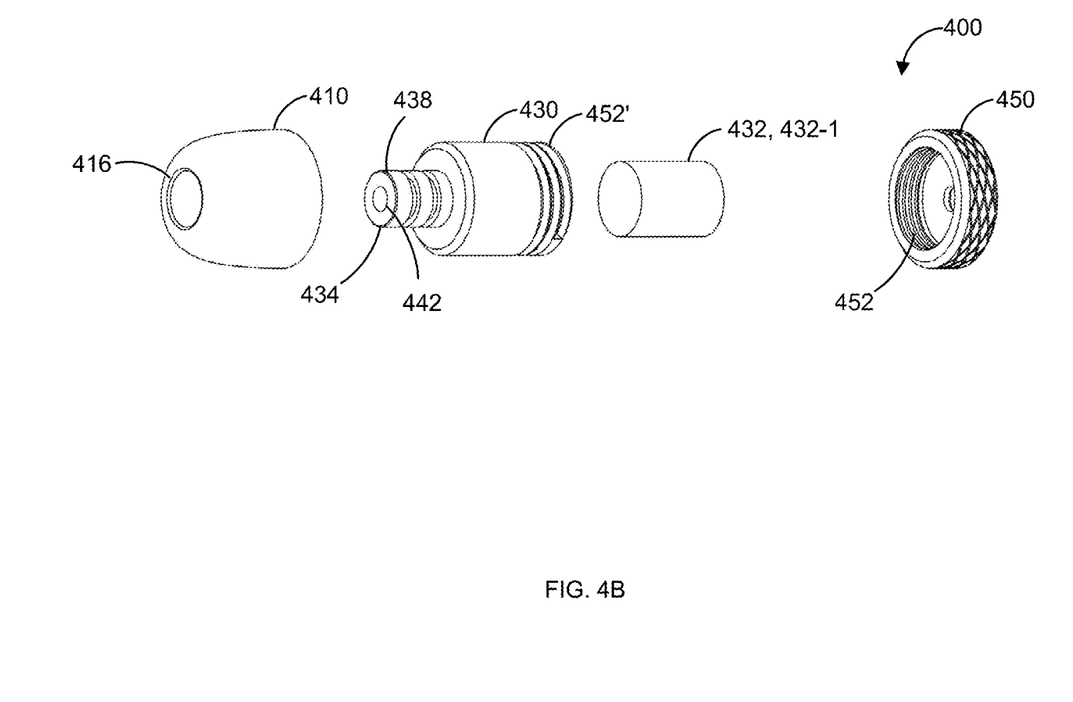

The housing 430 includes a hollow core 436 for receiving a sound attenuating capsule 432. The housing 430 of the present embodiment can be made of durable materials such as plastic or metal. The housing 430 of the present embodiment has an opening at each end to facilitate acoustic transmission. In particular, as shown in FIGS. 4A and 4B, the core 436 of housing 430 has an opening 440 at one end for receiving the sound attenuating capsule 432. Since the opening 440 is distal from the user's ear, opening 440 may be referred to as the distal opening. The core 436 extends toward the ear into a channel (not shown) within the attachment stem 434; this channel leads to an intermediate opening 442 (see FIG. 4B) located at the other end of the attachment stem 434. The intermediate opening 442 allows propagation of filtered sound to enter the ear piece 410 and ultimately to the user's ear via cavity 414 and second opening 416.

The sound attenuating capsule 432 can be enclosed in the housing 430 with the removable end cap 450, as seen in FIGS. 4A to 4F. The end cap 450 of the present embodiment includes a threaded securement mechanism with internal threads 452 to attach the end cap 450 to the housing 430 around the distal opening 440. The end cap 450 further includes an opening 454 to allow propagation of sound to the housing 430. In the present embodiment, the housing 430 is provided with corresponding external threads 452' on its external surface for engaging with the internal threads 452 of the end cap 450. The end cap 450 can therefore be secured to the housing 430 by twisting the end cap 450 in one direction to engage the matched internal and external threads 452, 452', and detached from the housing 430 by twisting the end cap 450 in the opposite direction. The outer surface of the end cap 450 can be textured to improve grip to enable the user to attach and detach the end cap 450 from the housing 430. In the illustrated embodiment of FIG. 4, for example, the end cap 450 is provided with a knurled finish to facilitate gripping.

The foregoing configuration allows a user to exchange one type of sound attenuating capsule 432 with another, as described in greater detail below. When a different sound attenuating capsule 432 is configured to provide different noise reduction performance or attenuation characteristics, a user can select the desired capsule that suits his or her needs or for the occasion. This selectability can optimize hearing quality and reduce the inconveniences of noisy environments. It may be appreciated from the foregoing that in some cases, the assembly may be prepackaged with an assortment of sound attenuating capsules for the user to choose from. In other cases, the user may obtain the various types of sound attenuating capsules separately, as desired.

Various types of sound attenuating capsules can be designed for the earplug assembly 400 or adapted for other embodiments such as assemblies 100 and 200 of FIGS. 1 and 2. For example, the sound attenuating capsule 432-1 of the assembly 400 shown in FIGS. 4A and 4B is embodied as a fiber tube capsule 432-1 shaped to fit within the housing 430. The fiber tube sound attenuating capsule 432-1 contains a soft foam core such as EVA (ethylene-vinyl acetate) foam for sound absorption to reduce the overall noise level for hearing protection, similar to foam earplugs used by construction workers. In some applications, the foam may be chosen so that it attenuates sound levels uniformly across the entire target audio spectrum. Various suitable absorption materials, or combinations of materials, may be used to fabricate the fiber tube sound attenuating capsule 432 to obtain different sound attenuation or filtering profiles.

Figure 4C:
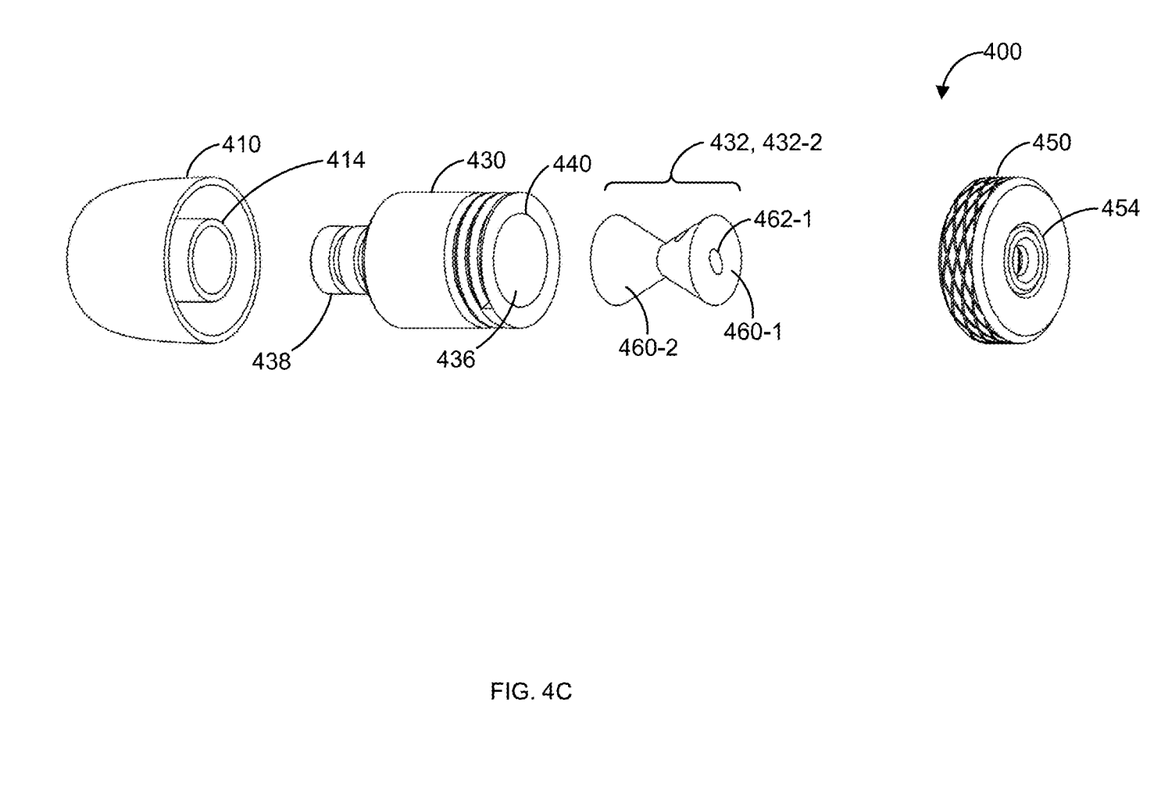
Figure 4D:
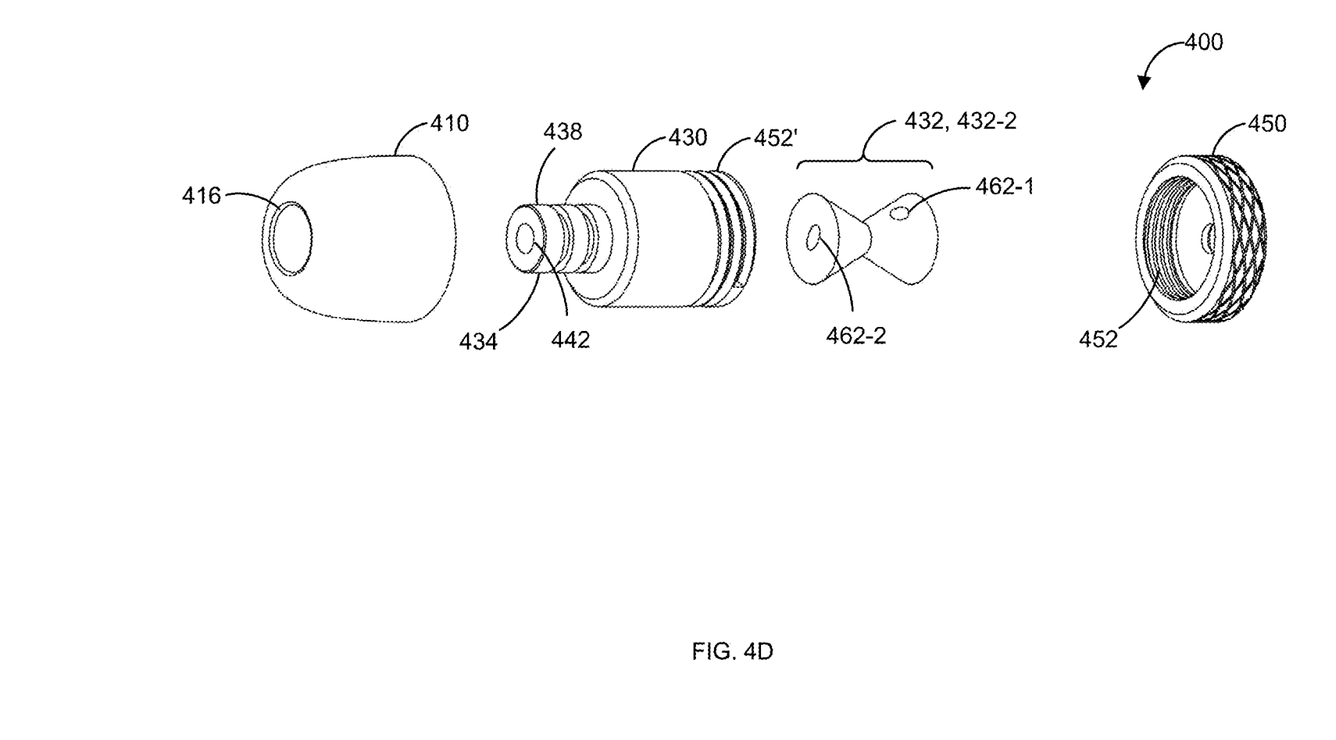

In the assembly 400 shown in FIGS. 4C and 4D, the sound attenuating capsule 432 is an inverted baffle cone 432-2. The illustrated embodiment is a double inverted baffle cone 432-2 (hereinafter the "baffle cone") comprising two cone portions 460-1 and 460-2 (collectively, "expansion chambers" 460) in which the "tail" or narrower part of one cone portion is attached to a corresponding narrower part of the other cone portion that results in an "hour-glass" structure with a narrow mid-section and wider end sections. In the present embodiment, the baffle cone 432-2 expansion chambers 460 are substantially the same in size, thereby forming a baffle cone 432-2 which is symmetrical in shape along its longitudinal axis and along its transverse mid-line. However, in other embodiments, the cone portions 460-1 and 460-2 that form the expansion chambers 460 may be sized and/or shaped differently so that the baffle cone 432-2 is not symmetrical. The baffle cone 432-2 can be made any suitable material capable of attenuating the desired sound frequencies. For example, in one embodiment, the baffle cone 432-2 is made of aluminum as it is generally strong and lightweight to provide both durability and comfort under extended use. However, other suitable materials that can be machined and refinished (e.g. deburred and drilled) such as aluminum alloy, brass, gold-plated brass, stainless steel, and the like can similarly be used.

Figure 5:
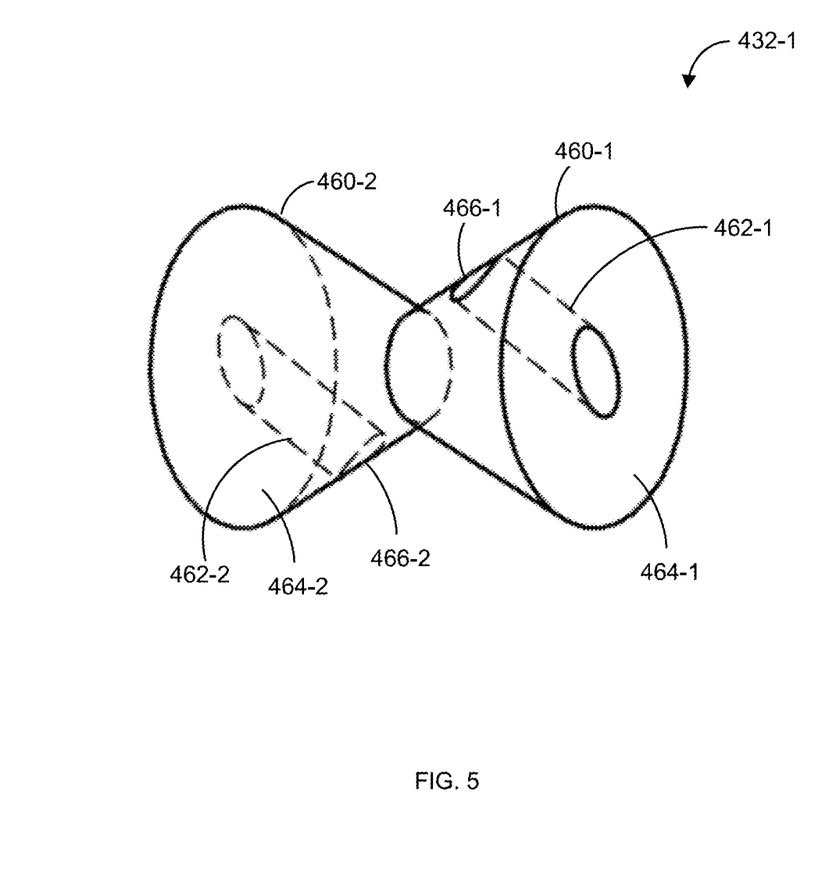
FIG. 5 shows an exemplary baffle cone that may be used as the noise reduction insert for the earplug assembly of FIG. 4.

In particular embodiments, each cone portion 460-1 and 460-2 of the baffle cone 432-2 includes at least one acoustic channel for the propagation of sound. Each cone portion may be solidly formed around the acoustic channel. FIG. 5 shows a close-up perspective view of the baffle cone 432-2 of FIG. 4C with one exemplary arrangement of the acoustic channels 462. These channels are intended to allow a certain range of noise to be audible and to allow an unmuffled quality of noise to be detected by the user, but at a reduced overall sound level to protect the user's hearing. As shown in FIG. 5, one acoustic channel 462-1 of cone portion 460-1 is positioned so that it extends between (and terminates at)

a planar or end face 464-1 and a side face 466-1 of cone portion 460-1. An acoustic channel 462-2 is positioned in a similar manner in cone portion 460-2, extending between a planar or end face 464-2 and side face 466-2 of cone portion 460-2. Each acoustic channel 462-1, 462-2 extends through its respective cone portion 460-1, 460-2, but does not extend into its neighboring or joined cone portion.

Based on the foregoing configuration, the acoustic profile of the baffle cone 432-2 can be tuned by adjusting the positioning of the acoustic channels 462 to direct sound into and out of the expansion chambers 460 to achieve the desired acoustic conditioning (i.e. to attenuate sound or noise of a certain frequency). The placement of and number of channels per expansion chamber 460 and/or hole and channel size within the expansion chamber 460 is directed to attenuation of a targeted frequency, thereby leaving other non-targeted frequencies unaffected. In other embodiments, each cone portion 460-1 and 460-2 may have a different number of acoustic channels 462 or different channel sizes. In yet other embodiments, one of the cone portions 460-1 and 460-2 may not have an acoustic channel 462, while the other does. In yet other embodiments, the expansion chambers do not include any acoustic channels.

Figure 4E:
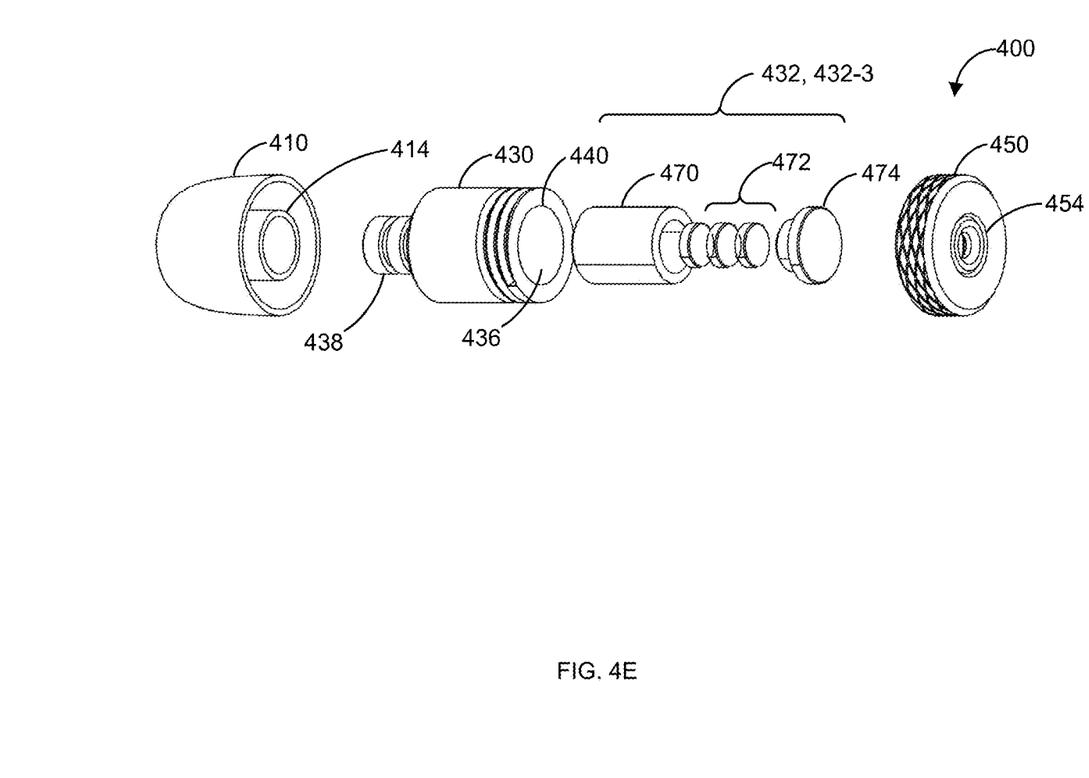
Figure 4F:
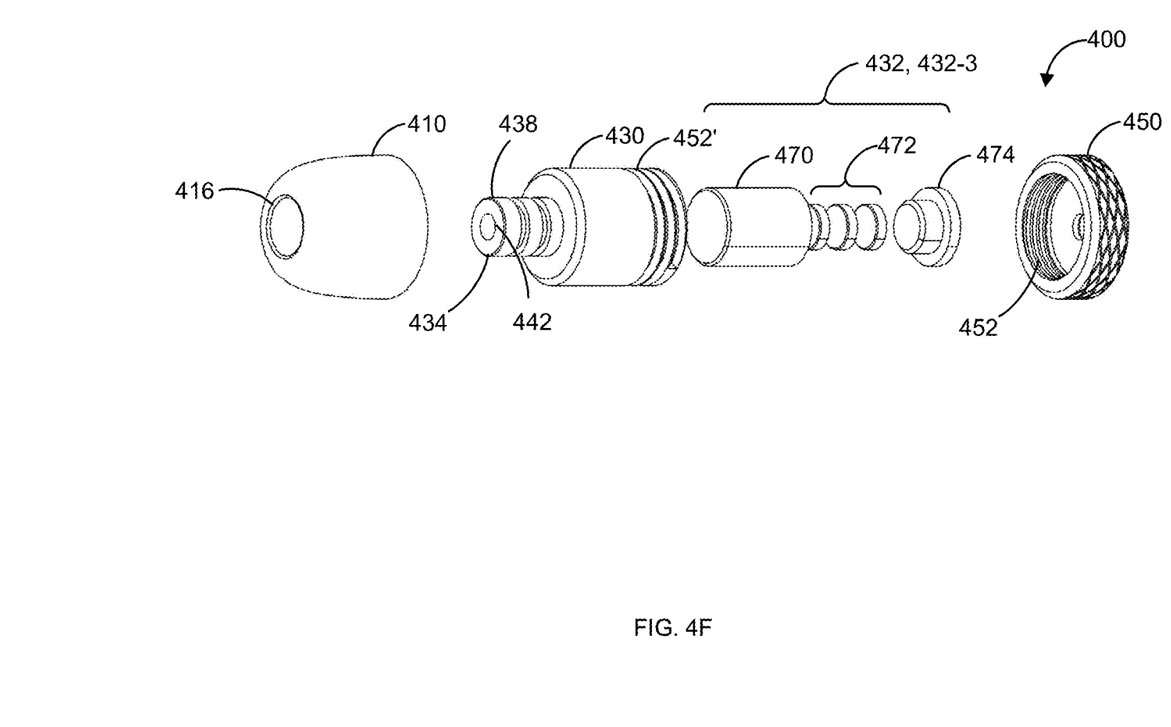

In the assembly 400 shown in FIGS. 4E and 4F, the sound attenuating capsule 432 is a combination capsule 432-3 comprising a capsule body 470 containing a filtering liquid (not shown), filtering elements 472 positioned within the capsule body 470, and a chamber closure 474 to enclose the liquid and filtering elements 472. In the illustrated embodiment, the filtering elements 472 comprise three rigid filtering plates within the capsule body 470. The filtering plates may be spaced evenly apart. The capsule body 470 and filtering plates are made of a suitable material, such as ABS (acrylonitrile butadiene styrene) plastic, to obtain the desired filtering properties. In other embodiments, the number of filtering plates can vary and their positioning can be varied to obtain different filtering properties. In one embodiment an oil, such as vegetable oil, is used as the liquid medium in the capsule body 470; however, in other embodiments other suitable liquids of various viscosities, including for example edible oils and water, can be used in the capsule body 470.

Acoustic attenuation can be used to evaluate noise reduction as a measure of the energy loss of sound propagation in media. Acoustic attenuation was measured for each of the assemblies of FIG. 4 using known standardized measurement protocols. The acoustic attenuation data shown in Table 1 below were obtained using the National Standard of the People's Republic of China GB 5893.4-86 UDC 614.89 (ear protector-earplugs). These results show that the above-described assemblies generally provide greater acoustic attenuation than a reference standard earplug within its class as well as some commercially available earplugs available to consumers (listed in the last 3 rows of Table 1). Assemblies using the combination capsule 432-3 resulted in the highest level of attenuation across the frequency range tested (63 Hz to 8000 Hz). The fiber core capsule 432-1 provided slightly less attenuation relative to the combination capsule 432-3 but had matching attenuation characteristics. The baffle cone 432-2 resulted in lower attenuation relative to the fiber core capsule 432-1 but still greater attenuation than the standard earplug. The attenuation performance of the combination capsule 432-3, fiber core capsule 432-1 and baffle cone 432-2, was generally the most strong between 500-4000 Hz. The response of the human ear to sound peaks at approximately 2500 to 3000 Hz. The human ear has a relatively low response at low frequencies. As such, the sound attenuation profile of the embodiments of FIG. 4, as indicated by the data of Table 1, covers the frequency range over which the human ear is most responsive to sound, so as to provide sound protection to the user.

TABLE 1

Sound attenuation of as a function of frequency

| Device | Freq. (Hz) | 63 | 125 | 250 | 500 | 1K | 2K | 3.15K | 4K | 6.3K | 8K |
|---|---|---|---|---|---|---|---|---|---|---|---|
| Combination capsule | Atten. (dB) | 29.1 | 29.3 | 29.5 | 30.1 | 33.1 | 35.8 | 36.8 | 29.9 | 29.2 | 29.5 |
| Baffle cone capsule | Atten. (dB) | 24.3 | 25.4 | 26.2 | 26.4 | 27.9 | 31.1 | 31.5 | 31.9 | 28.1 | 24.8 |
| Fiber core capsule | Atten. (dB) | 28.3 | 28.5 | 28.9 | 29.2 | 31.1 | 32.1 | 33.1 | 29.1 | 25.2 | 25.1 |
| Standard earplug | Atten. (dB) | 10 | 10 | 10 | 10 | 15 | 20 | 20 | 25 | / | / |
| 3M ™ E-A-R ™ HiFi ™ | Atten. (dB) | / | 14.5 | 15.3 | 16.9 | 18.9 | 22.5 | 23.0 | 19.8 | 22.3 | 24.6 |
| Vibes ™ Hi-Fidelity Earplugs | Atten. (dB) | / | 15.8 | 16.3 | 19.1 | 22.1 | 25.1 | / | 24 | / | 24.6 |
| Eargasm ™ High Fidelity Earplugs | Atten. (dB) | / | 28.6 | 24.5 | 27.2 | 29.5 | 33.4 | 29.8 | 28.6 | 31.3 | 34.2 |

The earplug assemblies described herein can be provided in a kit including a carrying case, various sizes of ear fitting tips (e.g. small, medium, and large), and various interchangeable filter elements for each earplug (e.g. fiber tube capsule 432-1, baffle cone 432-2, and combination capsule 432-3).

The examples and corresponding diagrams used herein are for illustrative purposes only. Different configurations and terminology can be used without departing from the principles expressed herein.

Although the invention has been described with reference to certain specific embodiments, various modifications thereof will be apparent to those skilled in the art without departing from the scope of the invention. The scope of the claims should not be limited by the illustrative embodiments set forth in the examples, but should be given the broadest interpretation consistent with the description as a whole.

The invention claimed is:

1. An earplug assembly for insertion into an ear canal of a user, the earplug assembly comprising:
    an ear piece comprising a first end shaped for insertion into the ear canal, and an opposing second end for receiving sound;
    a housing removably attached to the second end of the ear piece;
    a sound-selective sound barrier comprising at least one sound filtering element, wherein a hollow core is defined in the housing and is adapted to receive the sound-selective sound barrier; and
    an end cap attachable to the housing to enclose the sound-selective sound barrier in the housing, wherein the housing is positioned between the ear piece and the end cap, and wherein the at least one sound filtering element is selected from a group of sound filtering elements comprising an inverted baffle cone comprising two cone portions arranged in an hour-glass structure.

2. The earplug assembly of claim 1, wherein the ear piece is resiliently deformable.

3. The earplug assembly of claim 1, wherein the group of sound filtering elements comprises at least one of a solid sound attenuator and a liquid sound attenuator.

4. The earplug assembly of claim 3, wherein the group of sound filtering elements comprises a solid disc-shaped sound attenuator.

5. The earplug assembly of claim 3, wherein the group of sound filtering elements comprises a solid spherical sound attenuator.

6. The earplug assembly of claim 1, wherein the sound-selective sound barrier comprises a cartridge enclosing the at least one sound filtering element, the cartridge being removable from the housing.

7. An earplug assembly for insertion into an ear canal of a user, the earplug assembly comprising:
    a resiliently deformable ear piece comprising a first end shaped for insertion into the ear canal, and an opposing second end for receiving sound;
    a sealable body attachable to the ear piece;
    a first sound-selective sound attenuating capsule adapted for insertion into the sealable body; and
    a cap for sealingly enclosing the first sound attenuating capsule inside the body, wherein the cap is removable to allow the first sound attenuating capsule to be removed from the body to be replaced with a second sound attenuating capsule having a different attenuation profile, wherein the first sound attenuating capsule comprises an inverted baffle cone comprising two cone portions arranged in an hour-glass structure.

8. The earplug assembly of claim 7, wherein the cap comprises a threaded surface for engaging with a corresponding threaded surface on the body to couple the cap to the body.

9. The earplug assembly of claim 7, wherein the second sound attenuating capsule is a fiber tube capsule adapted for absorbing sound.

10. The earplug assembly of claim 9, wherein the fiber tube capsule comprises a foam core.

11. The earplug assembly of claim 7, wherein the inverted baffle cone is formed of aluminum.

12. The earplug assembly of claim 7, wherein the inverted baffle cone is formed of gold-plated brass.

13. The earplug assembly of claim 7, wherein in each cone portion of the inverted baffle cone, at least one hollow acoustic channel extends from an end face to a side face of the cone portion.

14. The earplug assembly of claim 7, wherein the second sound attenuating capsule is a combination capsule comprising a combination of at least one solid filtering element and at least one liquid sound filtering element enclosed within a capsule body.

15. The earplug assembly of claim 14, wherein the at least one solid sound filtering element comprises a plurality of rigid filter plates.

16. The earplug assembly of claim 14, wherein the at least one liquid sound filtering element comprises oil.

17. A kit for a pair of earplug assemblies, each earplug assembly in the kit comprising:
    an ear piece comprising a first end shaped for insertion into the ear canal, and an opposing second end for receiving sound;
    a housing removably attached to the second end of the ear piece, wherein a hollow core is defined in the housing;
    a plurality of interchangeable sound-selective sound attenuating capsules, wherein each one of the plurality of sound-selective sound attenuating capsules is insertable into the hollow core of the housing and has a sound attenuation profile that is different from other capsules in the plurality of sound-selective sound attenuating capsules, wherein at least one of the sound-selective sound attenuating capsules comprises an inverted baffle cone comprising two cone portions arranged in an hour-glass structure; and
    an end cap removably attachable to the housing to enclose a selected one of the plurality of sound-selective sound attenuating capsules within the housing.

* * * * *